United States Patent [19]

Westrup et al.

[11] Patent Number: 4,613,575

[45] Date of Patent: Sep. 23, 1986

[54] INDICATOR FOR DETERMINING ORGANIC ISOCYANATES ON A CARRIER

[75] Inventors: Bernhard Westrup; Joachim Marcoll, both of Lubeck, Fed. Rep. of Germany

[73] Assignee: Dragerwerk Aktiengesellschaft, Fed. Rep. of Germany

[21] Appl. No.: 707,520

[22] Filed: Mar. 4, 1985

[30] Foreign Application Priority Data

Mar. 2, 1984 [DE] Fed. Rep. of Germany ....... 3407687

[51] Int. Cl.[4] ............................................. G01N 31/22
[52] U.S. Cl. .................................... 436/106; 436/109; 436/127; 436/145; 422/56; 422/57; 422/86; 422/87; 422/61
[58] Field of Search ............... 436/106, 109, 127, 145; 422/56, 57, 86, 87

[56] References Cited

U.S. PATENT DOCUMENTS 3,533,750 10/1970 Belisle ................................. 436/109
4,416,966 11/1983 Sanders et al. ................. 430/235 X

FOREIGN PATENT DOCUMENTS 1163647 9/1969 United Kingdom ................ 436/109
515992 6/1976 U.S.S.R. .............................. 436/109

OTHER PUBLICATIONS

Tsigin et al., Spectrophotometric Determination of Isocyanates, Ind. Lab., 44(7), (1978), pp. 921-922.
Foliforova et al., Separate Determination of Residual Isocyanate Groups and Allophanates in Polyurethans, Ind. Lab., 41(6), (1975), pp. 825-827.

Primary Examiner—Barry S. Richman
Assistant Examiner—Jill Johnston
Attorney, Agent, or Firm—McGlew and Tuttle

[57] ABSTRACT

Organic isocyanates are detected with an indicator comprising bis-4-(dimethylamino)-phenyl-methylenimine-hydrochloride provided on a carrier along with a catalyst for its reaction with the organic isocyanates contained in a tested gas. Through an acid developer brought subsequently into contact with the indicator, this reaction occurs and thus the concentration of the organic isocyanates is made evident by a red coloration of the indicator.

13 Claims, No Drawings

INDICATOR FOR DETERMINING ORGANIC ISOCYANATES ON A CARRIER

FIELD AND BACKGROUND OF THE INVENTION

The present invention relates in general to indicators which can be used to indicate the presence of selected gases, and in particular to a new and useful indicator for organic isocyanates.

Organic isocyanates belong to the more important basic substances for producing plastics and foam materials. Because of their high toxicity, the air at the working places where isocyanate is produced and further treated must be carefully monitored.

One monitoring technique which is used during the production of toluylene diisocyanate, comprises directing a certain volume of the air to be tested through a prepared test paper and comparing the coloration with standard colors. The test paper used in this case is impregnated with a solution of 5-hydroxy-3',4'-benzocarbazole-4-carboxy-p-anisidide, soluble nitrite, a buffer, dialkylphtalate in methyl alcohol, and water after which the paper is dried. A paper so prepared is exposed to the tested air. The evaluated coloration determines the concentration (British Pat. No. 1,163,647).

This prior art test paper is applicable only to toluylene diisocyanate which was earlier primarily in use. Other isocyanates cannot be tested. The life of such a paper is very short. With a storage in complete darkness, such as in a blackened bottle, the life does not exceed 3 months.

SUMMARY OF THE INVENTION

The present invention is directed to an indicator of this kind having a long life and being insensitive to amines which are produced from isocyanates through hydrolysis.

Accordingly, an object of the present invention is to provide an indicator for determining the presence of organic isocyanates, and a method for determining the presence of organic isocyanates which utilizes a carrier for a receiving air to be tested and which carries bis-4-(dimethylamino)-phenyl-methylenimine-hydrochloride, plus a catalyst for its reaction with organic isocyanate and a developer which is applied to the carrier after its exposure to the air to be tested for causing a coloration of the carrier which coloration is a measurement of the organic isocyanates present.

A further object of the present invention is to use a non-volatile basic nitrogen compound for the catalyst such as tertiary amine or quaternary ammonium salt. The developer may be in the form of acid such as acetic acid and the carrier may be paper, plastic foil or silica gel.

The method of the invention includes exposing test gas to bis-4-(dimethylamino)-phenyl-methylenimine-hydrochloride, in the presence of a catalyst and on a carrier with a subsequent exposure of the carrier to a developer for producing a coloration of the carrier which is indicative of the presence of organic isocyanates.

The various features of novelty which characterize the invention are pointed out with particularity in the claims annexed to and forming a part of this disclosure.

DESCRIPTION OF THE PREFERRED EMBODIMENTS

The inventive indicator is based on the reaction of bis-4-(dimethylamino)-phenyl-methylenimine-hydrochloride with isocyanates. The speed of this reaction strongly depends on catalytic effects. Non-volatile basic nitrogen compounds may serve as suitable catalysts. Due to the reaction of methylenimine-hydrochloride with an organic isocyanate in the presence of a catalyst, a colorless to slightly yellowish compound is obtained. By protonation through the developer the compound turns deeply red to violet and thus becomes very detectable in opto-electronic ways. The degree of coloration is an indirect measure of the isocyanate concentration in the tested air.

If used in a gas measuring apparatus, the indicator to be exposed to the tested air, must initially be made slightly alkaline through the catalyst, and then made slightly acid. For this purpose, liquid acid is sprayed on the indicator.

If organic isocyanates are present in the air, the indicator takes on a red color.

A paper, silica gel, plastic foil or other carrier is provided which carries the catalyst and methylenimine-hydrochloride and which, after exposure to the test air or medium, is provided with the developer. Thus, the indicator may be provided as a kit comprising the carrier which includes the catalyst and the methyleneimine-hydrochloride as one component of the kit, and the developer, e.g. acidic developer, as the other component thereof.

The invention offers the advantage that due to the two-stage exposure to gas and development, the organic isocyanate is detected directly. This detection is based on the direct reaction exclusively of the non-decomposed isocyanate. A simultaneous amine content in the air, produced by the decomposition of isocyanates, is not detected. Conventional colorimetric methods based on the detection of these amines formed through hydrolysis, require a double determination if also the free active isocyanate is to be detected. The organic residue of the isocyanate is not a component of the chromogenic system. The indicator is therefore sensitive also to aliphatic isocyanates where other colorimetric methods fail.

While specific embodiments of the invention have been shown and described in detail to illustrate the application of the principles of the invention, it will be understood that the invention may be embodied otherwise without departing from such principles.

What is claimed is:

1. Indicator kit for detecting organic isocyanates in a test medium, comprising a carrier for receiving a test medium, said carrier having supported thereon bis-4-(dimethylamino)-phenyl-methyleneimine-hydrochloride plus a non-volatile basic nitrogen compound as catalyst for its reaction with organic isocyanates to form a compound, as one component of the kit, and an acidic developer, as the other component of the kit, and the acidic developer being applicable to the carrier to react with the formed compound and produce a coloration which is indicative of the presence of organic isocyanates in the test medium.

2. Kit of claim 1, wherein the catalyst is a tertiary amine.

3. Kit of claim 1, wherein the catalyst is a quaternary ammonium salt.

4. Kit of claim 1, wherein the developer comprises acetic acid.

5. Kit of claim 1, wherein the carrier is made of paper.

6. Kit of claim 1, wherein the carrier is made of plastic foil.

7. Kit of claim 1, wherein the carrier is made of silica gel.

8. Indicator kit for detecting organic isocyanates in a test medium, comprising as one component of the kit a carrier selected from the group consisting of paper, plastic foil and silica gel, for receiving the test medium and having supported thereon bis-4-(dimethylamino)-phenyl-methyleneimine-hydrochloride plus a non-volatile basic nitrogen compound as catalyst for its reaction with organic isocyanates to form a compound, and as the other component of the kit an acidic developer appliable to the carrier to react with the formed compound and produce a coloration which is indicative of the presence of organic isocyanates in the medium.

9. Kit of claim 8, wherein the acid is acetic acid.

10. Method of indicating the presence of organic isocyanates in a test medium using the kit of claim 8, comprising passing the test medium to said one component for reacting said hydrochloride with organic isocyanates to form a compound, and applying said other component to said one component after it has been exposed to the test medium to produce a color reaction with the formed compound, the color reaction being indicative of the presence of organic isocyanates.

11. Method of claim 10, wherein said other component is acetic acid.

12. Method of indicating the presence of organic isocyanates in a test medium, comprising passing the test medium to a carrier having supported thereon bis-4-(dimethylamino)-phenyl-methyleneimine-hydrochloride plus a non-volatile basic nitrogen compound as catalyst for reacting it with organic isocyanates to form a compound, and applying an acidic developer to the carrier after it has been exposed to the test medium to produce a color reaction with the formed compound, the color reaction being indicative of the presence of organic isocyanates.

13. Method of claim 12, including applying acetic acid to the carrier as the developer.

* * * * *